United States Patent
Knodel

(10) Patent No.: US 8,496,155 B2
(45) Date of Patent: *Jul. 30, 2013

(54) SURGICAL STAPLER WITH ANGLED FEEDER BELTS

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,916

(22) Filed: Dec. 2, 2011

(65) Prior Publication Data

US 2012/0074202 A1 Mar. 29, 2012

Related U.S. Application Data

(63) Continuation of application No. 12/781,746, filed on May 17, 2010, now Pat. No. 8,070,034.

(60) Provisional application No. 61/182,528, filed on May 29, 2009.

(51) Int. Cl.
*A61B 17/04* (2006.01)
*A61B 17/10* (2006.01)

(52) U.S. Cl.
USPC .................................. 227/176.1; 227/175.1

(58) Field of Classification Search
USPC ....... 227/175.1–182.1, 19, 132–134; 606/219
See application file for complete search history.

(56) References Cited

U.S. PATENT DOCUMENTS

| | | | |
|---|---|---|---|
| 2,127,665 A * | 8/1938 | Leslie | 29/413 |
| 3,581,551 A | 6/1971 | Wilkinson | |
| 3,650,453 A | 3/1972 | Smith, Jr. | |
| 3,675,688 A | 7/1972 | Bryan et al. | |
| 3,822,818 A * | 7/1974 | Strekopytov et al. | 227/124 |
| 3,899,914 A | 8/1975 | Akiyama | |
| 3,955,581 A | 5/1976 | Spasiano et al. | |
| 4,086,926 A | 5/1978 | Green et al. | |
| 4,167,229 A * | 9/1979 | Keusch et al. | 206/343 |
| 4,212,094 A * | 7/1980 | Pray | 24/31 B |
| 4,228,895 A | 10/1980 | Larkin | |
| 4,275,813 A | 6/1981 | Noiles | |

(Continued)

FOREIGN PATENT DOCUMENTS

| EP | 1238634 | 9/1994 |
|---|---|---|
| EP | 1464287 | 10/2004 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Robert Long
(74) *Attorney, Agent, or Firm* — Cardica, Inc.

(57) ABSTRACT

An exemplary surgical stapler may include a staple holder, including an upper surface with two substantially-planar angled surfaces positioned lateral to and angled relative to each other. The staple holder may include staple channels within it, and each staple channel may open to a corresponding angled surface. The stapler may also include at least one feeder belt extending into the staple holder and staples frangibly affixed to the feeder belt. Generally, at least one staple is held within a corresponding staple channel of the staple holder.

14 Claims, 2 Drawing Sheets

U.S. PATENT DOCUMENTS

| | | | |
|---|---|---|---|
| 4,475,679 A | 10/1984 | Fleury, Jr. | |
| 4,589,416 A * | 5/1986 | Green | 606/220 |
| 4,617,928 A * | 10/1986 | Alfranca | 227/180.1 |
| 4,619,393 A * | 10/1986 | Maurer | 227/136 |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |
| 4,969,591 A | 11/1990 | Richards et al. | |
| 4,978,049 A | 12/1990 | Green | |
| 5,156,315 A | 10/1992 | Green et al. | |
| 5,170,925 A | 12/1992 | Madden et al. | |
| 5,192,288 A | 3/1993 | Thompson et al. | |
| 5,242,457 A * | 9/1993 | Akopov et al. | 606/144 |
| 5,307,976 A | 5/1994 | Olson et al. | |
| 5,413,272 A | 5/1995 | Green et al. | |
| 5,476,206 A | 12/1995 | Green | |
| 5,542,323 A * | 8/1996 | Habermehl et al. | 81/434 |
| 5,547,117 A | 8/1996 | Hamblin et al. | |
| 5,553,765 A | 9/1996 | Knodel et al. | |
| 5,582,611 A * | 12/1996 | Tsuruta et al. | 606/46 |
| 5,620,289 A | 4/1997 | Curry | |
| 5,630,541 A | 5/1997 | Williamson, IV et al. | |
| 5,653,373 A * | 8/1997 | Green et al. | 227/175.1 |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,833,695 A * | 11/1998 | Yoon | 606/139 |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 5,974,918 A * | 11/1999 | Nakagawa et al. | 81/434 |
| 6,306,149 B1 | 10/2001 | Meade | |
| 6,391,038 B2 | 5/2002 | Vargas et al. | |
| 6,419,682 B1 | 7/2002 | Appleby et al. | |
| 6,478,804 B2 * | 11/2002 | Vargas et al. | 606/153 |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,779,959 B1 * | 8/2004 | Yang | 411/443 |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,070,083 B2 * | 7/2006 | Jankowski | 227/176.1 |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,217,285 B2 * | 5/2007 | Vargas et al. | 623/1.36 |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,422,138 B2 * | 9/2008 | Bilotti et al. | 227/179.1 |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 7,828,188 B2 | 11/2010 | Jankowski | |
| 7,918,376 B1 * | 4/2011 | Knodel et al. | 227/175.1 |
| 7,954,683 B1 * | 6/2011 | Knodel et al. | 227/175.1 |
| 7,963,432 B2 * | 6/2011 | Knodel et al. | 227/175.1 |
| 7,988,026 B2 * | 8/2011 | Knodel et al. | 227/175.1 |
| 8,070,034 B1 * | 12/2011 | Knodel | 227/176.1 |
| 8,328,062 B2 * | 12/2012 | Viola | 227/179.1 |
| 8,365,971 B1 * | 2/2013 | Knodel | 227/175.1 |
| 2003/0035702 A1 * | 2/2003 | Lin | 411/442 |
| 2003/0120284 A1 | 6/2003 | Palacios et al. | |
| 2003/0178465 A1 * | 9/2003 | Bilotti et al. | 227/180.1 |
| 2003/0236551 A1 | 12/2003 | Peterson | |
| 2005/0033329 A1 * | 2/2005 | Bombard et al. | 606/153 |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0241660 A1 * | 10/2006 | Bombard et al. | 606/153 |
| 2006/0253143 A1 | 11/2006 | Edoga | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0114261 A1 * | 5/2007 | Ortiz et al. | 227/175.1 |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0087707 A1 * | 4/2008 | Jankowski | 227/176.1 |
| 2008/0190990 A1 * | 8/2008 | Holsten et al. | 227/176.1 |
| 2008/0272175 A1 | 11/2008 | Holsten et al. | |
| 2009/0277949 A1 * | 11/2009 | Viola et al. | 227/178.1 |
| 2010/0019014 A1 * | 1/2010 | Rodenhouse | 227/32 |
| 2010/0089973 A1 * | 4/2010 | Kostrzewski | 227/180.1 |
| 2010/0187285 A1 * | 7/2010 | Harris et al. | 227/179.1 |
| 2010/0191255 A1 * | 7/2010 | Crainich et al. | 606/142 |
| 2010/0191282 A1 * | 7/2010 | Harris et al. | 606/219 |
| 2010/0213240 A1 | 8/2010 | Kostrzewski | |
| 2010/0320251 A1 * | 12/2010 | Leitner | 227/113 |
| 2011/0278343 A1 * | 11/2011 | Knodel et al. | 227/176.1 |
| 2012/0074202 A1 * | 3/2012 | Knodel | 227/180.1 |

FOREIGN PATENT DOCUMENTS

| | | |
|---|---|---|
| EP | 1875868 A1 * | 1/2008 |
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449, (Apr. 29, 2009).

"International Search Report", PCT/US2008/075449, (Apr. 29, 2009).

"Written Opinion of the International Searching Authority", PCT/US2008/075449, (Apr. 29, 2009).

"Cardica Microcutter Implant Delivery Device 510(k), Cover Sheet, Table 10.1, "Substantial Equivalence Comparison," and Section 12, "Substantial Equivalence Discussion"".

* cited by examiner

SURGICAL STAPLER WITH ANGLED FEEDER BELTS

This application is a continuation of U.S. patent application Ser. No. 12/781,746, filed on May 17, 2010, which claimed priority to U.S. Provisional Patent Application Serial No. 61/182,528, filed on May 29, 2009, each and every one of which is herein incorporated by reference in its entirety.

FIELD OF THE INVENTION

The invention generally relates to surgical staplers and stapling.

BACKGROUND

Surgical staplers for use in minimally invasive surgery may be designed to be generally cylindrical in shape in order to fit through a corresponding trocar port placed in a patient, where that trocar port has a generally circular orifice defined therethrough. Such a surgical stapler typically includes a staple holder and an anvil pivotally connected to the staple holder. Referring to FIG. 1, a staple holder 2 viewed in cross-section may be generally shaped as a segment of a circle defined by a chord, which is the upper surface 4 of the staple holder 2 through which staples are ejected. Staples are held in individual bays or channels 6 within the staple holder 2. The bays or channels 6 are oriented perpendicular to the upper surface 4 of the staple holder 2. Consequently, the bays or channels 6 are oriented parallel to one another. Similarly, a knife slot 8 is typically defined in the staple holder 2, where that knife slot 8 is also oriented perpendicular to the upper surface 4 of the staple holder 2. The perpendicularity of the bays or channels 6 to the upper surface 4 limits the size of staples that can be deployed from the staple holder 2, because as the bays or channels 6 increase in size, they must move inward laterally such that they can still fit inside the staple holder 2. Further, by moving the bays or channels 6 laterally inward, space within the staple holder 2 laterally outward from those bays or channels 6 is wasted.

BRIEF DESCRIPTION OF THE DRAWINGS

The use of the same reference symbols in different figures indicates similar or identical items.

DETAILED DESCRIPTION

Figure 1:
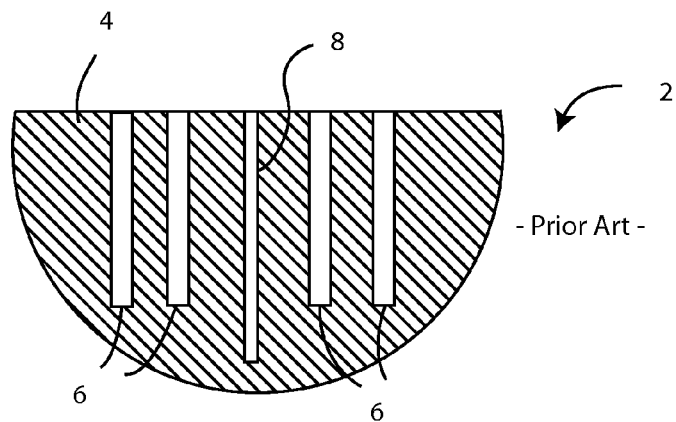
FIG. 1 is a cross-section end view of a prior art staple holder.
Figure 2:
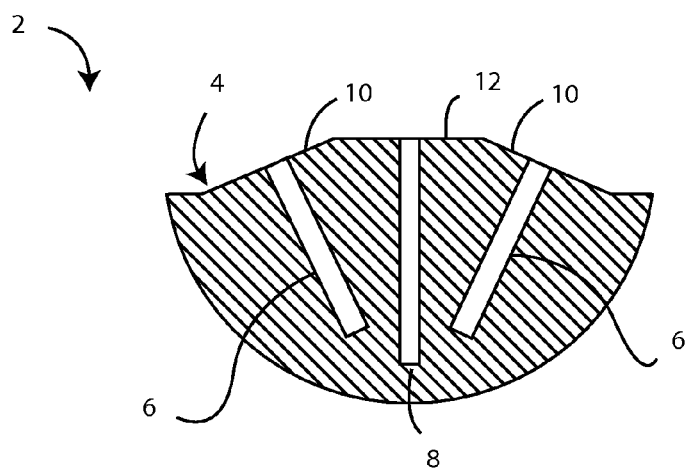
FIG. 2 is a cross-section end view of an exemplary staple holder with angled staple bays.

Referring to FIG. 2, a staple holder 2 may have an upper surface 4 that includes two angled surfaces 10. Each angled surface 10 is positioned lateral to the other. Each angled surface 10 may lie substantially in a different plane than the other, such that the two planes intersect. The upper surface 4 also may include a plateau surface 12 that connects the two angled surfaces 10. The angled surfaces 10 each may form an angle with the plateau surface 12. Alternately, the plateau surface 12 may be omitted, and the two angled surfaces 10 may directly intersect one another. At least one staple bay or channel 6 may be positioned relative to a corresponding angled surface 10 such that the upper end of that bay or channel 6 opens to that angled surface 10. Such a staple bay or channel 6 may be oriented substantially perpendicular to the angled surface 10, or may be oriented differently relative to the corresponding angled surface 10. Optionally, at least one staple bay or channel 6 may be oriented differently than at least one other staple bay or channel 6; the staple bays or channels 6 need not all have the same orientation relative to the angled surfaces 10 or each other. This angled orientation allows deeper staple bays or channels 6 to be defined in the staple holder 2 than in a staple holder 2 of the prior art of the same diameter. Further, the use of angled surfaces 10 increases the surface area of the upper surface 4 of the staple holder 2 as compared to the planar upper surface 4 of the prior art staple holder 2. In addition, by providing one or more bays or channels 6 in an angled configuration, those bays or channels 6 may be placed within the staple holder 2 in such a way that they can eject staples at a lateral distance further from the longitudinal center line of the staple holder 2 than the staple holders 2 of the prior art. Alternately, the staple holder 2 may have a substantially planar upper surface 4 such as shown in FIG. 1, and one or more staple bays or channels 6 may be oriented at an angle relative to that upper surface 4. At least one of the staple bays or channels 6 may form substantially a V-shape with regard to at least one other staple bay or channel 6 as viewed from the end. Optionally, a knife slot 8 may be defined in the staple holder 2, and may be located between staple bays or channels 6 as seen from the end.

Figure 3:
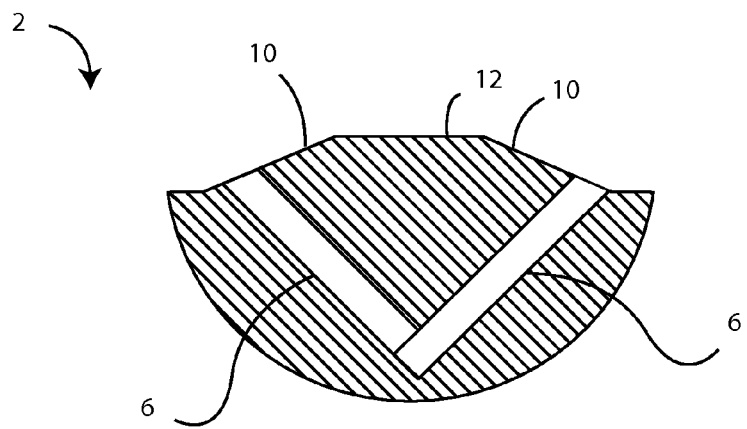
FIG. 3 is a cross-section end view of another exemplary staple holder with angled staple bays.

Referring also to FIG. 3, where staple bays 6 are used, the staple bays 6 may overlap one another as viewed from the end. Longitudinally, those staple bays 6 may be staggered to prevent interference between them. By overlapping two or more staple bays 6, even more efficiency may be obtained in the internal layout of the staple holder 2. In such a configuration, the knife slot 8 may be omitted, or if utilized, may be positioned above the staple bays 6 to prevent interference.

Figure 4:
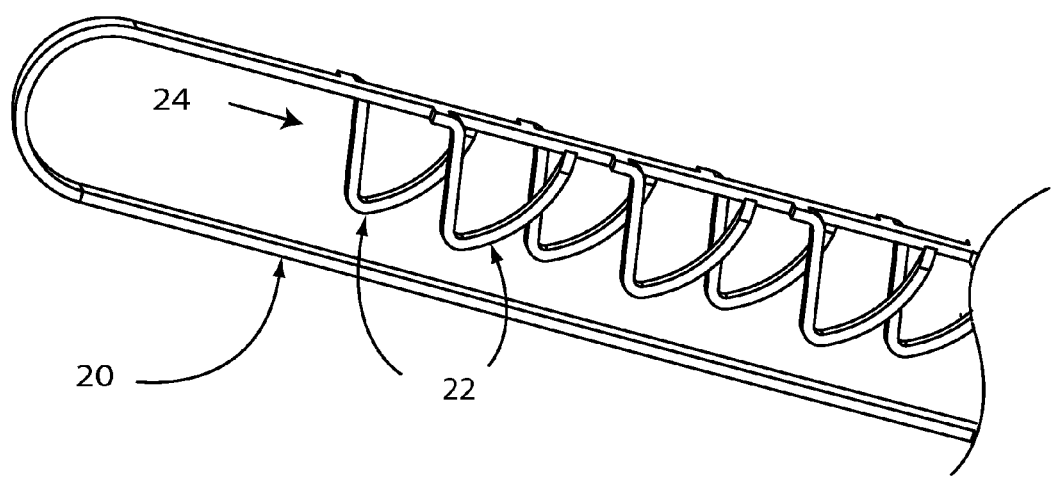
FIG. 4 is a perspective view of an exemplary feeder belt with staples frangibly affixed thereto.

Referring also to FIG. 4, any suitable staples, clips, or fasteners 22 may be ejected from the bays or channels 6. As one example, standard U-shaped or B-shaped staples or clips may be used. As another example, at least one feeder belt 20 with staples 22 fixed to and frangibly separable therefrom may be utilized; such a feeder belt 20 may be as described in U.S. Patent Application Publication No. 2009/0065552, published on Mar. 12, 2009, now U.S. Pat. No. 7,988,026, issued on Aug. 2, 2011, which is hereby incorporated by reference herein in its entirety. One or more rows 24 of staples 22 may be connected to the feeder belt 20, and each row 24 of staples 22 may be oriented generally longitudinally. Where a staple bay or channel 6 is oriented substantially perpendicular to the angled surface 10, as described above, the staples 22 are necessarily oriented substantially perpendicular to the angled surface 10. Where the staples 22 are oriented substantially perpendicular to the feeder belt 20, as described in U.S. Pat. No. 7,988,026, the feeder belt 20 is thus substantially parallel to the corresponding angled surface 10.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. A surgical stapler, comprising:
   a staple holder including an upper surface, said upper surface comprising two substantially-planar angled surfaces positioned lateral to and angled relative to each other;
   a plurality of staple channels within said staple holder, wherein each of said staple channels opens to one of said angled surfaces, and wherein said staple channels lie in different planes relative to one another;
   a feeder belt comprises at least one loop extending into said staple holder along a different plane from any of the planes along which said staple channels lie; and
   a plurality of staples frangibly affixed to said feeder belt, wherein at least one of said staples is held within one of said staple channels.

2. The surgical stapler of claim 1, wherein said feeder belt is substantially parallel to a corresponding said angled surface.

3. The surgical stapler of claim 1, wherein said angled surfaces lie in two different intersecting planes.

4. The surgical stapler of claim 3, wherein said planes intersect above a longitudinal centerline of said staple holder.

5. The surgical stapler of claim 3, wherein said planes intersect above the upper surface of said staple holder.

6. The surgical stapler of claim 1, wherein said angled surfaces face away from one another.

7. The surgical stapler of claim 1, wherein said angled surfaces form an obtuse angle relative to one another, as measured about a longitudinal axis of said staple holder and through said staple holder.

8. The surgical stapler of claim 1, further comprising a plateau surface between said angled surfaces, which connects said angled surfaces.

9. The surgical stapler of claim 1, wherein at least one of said staple channels is oriented substantially perpendicular to a corresponding one of said angled surfaces.

10. The surgical stapler of claim 1, wherein at least two of said staple channels overlap one another as viewed along the longitudinal axis of said staple holder.

11. The surgical stapler of claim 1, further comprising a longitudinally-extending knife slot defined in said staple holder, said knife slot located laterally between at least two of said staple channels.

12. The surgical stapler of claim 1, wherein at least one of said staple channels is oriented in a different direction than at least one other of said staple channels.

13. The surgical stapler of claim 1, wherein said staple channels substantially form a V-shape as viewed along a longitudinal axis of said staple holder.

14. The surgical stapler of claim 1, wherein said plurality of staples is arranged in at least one longitudinally-extending row along said feeder belt.

* * * * *